US012693216B2

(12) United States Patent
Yeh et al.

(10) Patent No.: US 12,693,216 B2
(45) Date of Patent: Jul. 28, 2026

(54) OPTICAL SENSOR DEVICE FOR HYDRATION MEASUREMENT

(71) Applicant: Artilux, Inc., Menlo Park, CA (US)

(72) Inventors: Chih-Wei Yeh, Hsinchu County (TW); Chun-Wei Lin, Hsinchu County (TW)

(73) Assignee: Artilux, Inc., Menlo Park, CA (US)

( * ) Notice: Subject to any disclaimer, the term of this patent is extended or adjusted under 35 U.S.C. 154(b) by 156 days.

(21) Appl. No.: 18/886,409

(22) Filed: Sep. 16, 2024

(65) Prior Publication Data

US 2025/0110048 A1 Apr. 3, 2025

Related U.S. Application Data

(60) Provisional application No. 63/587,157, filed on Oct. 2, 2023.

(51) Int. Cl.
*G01N 21/3554* (2014.01)
*A61B 5/00* (2006.01)
*G01N 21/3563* (2014.01)

(52) U.S. Cl.
CPC ....... *G01N 21/3554* (2013.01); *A61B 5/0082* (2013.01); *A61B 5/4875* (2013.01); *G01N 21/3563* (2013.01); *A61B 2560/0223* (2013.01); *G01N 2201/127* (2013.01)

(58) Field of Classification Search
CPC ........... G01N 21/3554; G01N 21/3563; G01N 2201/127; A61B 5/0082; A61B 5/4875; A61B 2560/0223; A61B 5/1455; A61B 5/443; A61B 5/0075
See application file for complete search history.

(56) References Cited

U.S. PATENT DOCUMENTS

| | | |
|---|---|---|
| 10,206,619 B1 | 2/2019 | Lee et al. |
| 11,547,331 B1 * | 1/2023 | Sharifzadeh ......... A61B 5/1455 |
| 2020/0383628 A1 | 12/2020 | Borremans et al. |
| 2022/0008000 A1 | 1/2022 | Varghese et al. |
| 2022/0401014 A1 | 12/2022 | Han et al. |

* cited by examiner

*Primary Examiner* — Kiho Kim
(74) *Attorney, Agent, or Firm* — Dority & Manning, P.A.

(57) ABSTRACT

An optical sensor device for determining a hydration level information of an object includes a light-emitting element, a light-receiving element, and an analyzer. The light-emitting element is configured to emit a first light at a first wavelength and a second light at a second wavelength. The light-receiving element is configured to receive a first reflected light at the first wavelength and a second reflected light at the second wavelength from the object. The analyzer is configured to perform a hydration measurement to determine the hydration level information. The hydration level information is based on: a first reference signal strength at the first wavelength and a second reference signal strength at the second wavelength obtained from the light-receiving element when the object is not present; and a first signal strength of the first reflected light and a second signal strength of the second reflected light when the object is present.

20 Claims, 7 Drawing Sheets

100

S501
OBTAIN REFERENCE SIGNAL STRENGTHS SS_REF(W1), SS_REF(W2) WHEN THE OBJECT IS NOT PRESENT

S503
OBTAIN REFLECTED SIGNAL STRENGTHS SS(W1), SS(W2) WHEN THE OBJECT IS PRESENT

S505
CALIBRATE AT LEAST ONE OF SS_REF(W1), SS_REF(W2), SS(W1), SS(W2) BY A CALIBRATE FACTOR

S507
DETERMINE THE HYDRATION LEVEL INFORMATION BY A MATHEMATICAL METHOD ACCORDING TO SS_REF(W1), SS_REF(W2), SS(W1), SS(W2)

600

600

OPTICAL SENSOR DEVICE FOR HYDRATION MEASUREMENT

RELATED APPLICATIONS

The subject application claims the benefit of priority to U.S. Provisional Patent Application No. 63/587,157 filed on Oct. 2, 2023, entitled "Optical Sensor Device for Hydration Measurement," which is incorporated by reference herein in its entirety for all purposes.

FIELD

The present disclosure relates generally to technology for use with optical sensor devices (e.g., object sensor devices for determining hydration measurements and related hydration information) and related applications.

BACKGROUND

Optical sensor devices are being used in many systems, such as smartphones, wearable electronics, robotics, and autonomous vehicles, etc. for proximity detection, 2D/3D imaging, object recognition, image enhancement, material recognition, color fusion, health monitoring, and other relevant applications. The optical sensor device can be operable for different wavelength ranges, including visible light (e.g., wavelength range 380 nm to 780 nm, or a similar wavelength range as defined by a particular application) and non-visible light. The non-visible light includes near-infrared (NIR, e.g., wavelength range from 780 nm to 1000 nm, or a similar wavelength range as defined by a particular application) and short-wavelength infrared (SWIR, e.g., wavelength range from 1000 nm to 3000 nm, or a similar wavelength range as defined by a particular application) light.

The hydration measurement for the skin is considered an essential factor in reflecting skin appearance and skin health. Various skin condition measuring apparatuses capable of measuring skin condition, such as stratum corneum hydration (SCH), transepidermal water loss (TEWL), etc., have been developed and commercialized. The present disclosure discloses an optical sensor device capable of providing hydration level information of an object, for example, skin hydration level information and monitoring the skin hydration of persons.

SUMMARY

Aspects and advantages of embodiments of the present disclosure will be set forth in part in the following description, or may be learned from the description, or may be learned through practice of the embodiments.

One example aspect of the present disclosure is directed to an optical sensor device for determining a hydration level information of an object. The optical sensor device includes a light-emitting element configured to emit a first light at a first wavelength and a second light at a second wavelength. The optical sensor device includes a light-receiving element configured to receive a first reflected light at the first wavelength and a second reflected light at the second wavelength from the object. The optical sensor device includes an analyzer configured to perform a hydration measurement to determine the hydration level information. Performing the hydration measurement includes obtaining a first reference signal strength at the first wavelength and a second reference signal strength at the second wavelength from the light-receiving element when the object is not present. Performing the hydration measurement includes obtaining a first signal strength of the first reflected light and a second signal strength of the second reflected light from the light-receiving element when the object is present. Performing the hydration measurement includes determining the hydration level information based on the first reference signal strength, the second reference signal strength, the first signal strength, and the second signal strength.

In some implementations, performing the hydration measurement further includes calibrating at least one of the first reference signal strength, the second reference signal strength, the first signal strength, and the second signal strength before determining the hydration level information.

In some implementations, the calibrating step uses a calibration factor to calibrate at least one of the first reference signal strength, the second reference signal strength, the first signal strength, and the second signal strength.

In some implementations, the first wavelength is different from the second wavelength.

In some implementations, the hydration level information is determined by a mathematical method.

In some implementations, the mathematical method is a curve fitting method.

In some implementations, the first wavelength and the second wavelength are within a short-wavelength infrared (SWIR) wavelength range.

In some implementations, the first wavelength is at approximately 1050 nm.

In some implementations, the second wavelength is at approximately 1450 nm.

In some implementations, an absorption coefficient of water at the second wavelength is higher than that at the first wavelength.

Another example aspect of the present disclosure is directed to a method of hydration measurement of an optical sensor device for an object. The method includes receiving, by a hydration measurement unit, a first reference signal strength at a first wavelength and a second reference signal strength at a second wavelength from a light-receiving element when the object is not present. The method includes receiving, by the hydration measurement unit, a first signal strength at the first wavelength and a second signal strength at the second wavelength from the light-receiving element when the object is present. The method includes determining, by the hydration measurement unit, a hydration level information based on the first reference signal strength, the second reference signal strength, the first signal strength, and the second signal strength.

In some implementations, the method further includes calibrating at least one of the first reference signal strength, the second reference signal strength, the first signal strength, and the second signal strength before the determining step.

In some implementations, the calibrating step uses a calibration factor to calibrate at least one of the first reference signal strength, the second reference signal strength, the first signal strength, and the second signal strength.

In some implementations, the hydration level information is determined by a mathematical method.

In some implementations, the mathematical method is curve fitting method.

In some implementations, the first wavelength and the second wavelength are within a short-wavelength infrared (SWIR) wavelength range.

In some implementations, the first wavelength is at approximately 1050 nm.

In some implementations, the second wavelength is at approximately 1450 nm.

In some implementations, an absorption coefficient of water at the second wavelength is higher than that at the first wavelength.

In some implementations, the first wavelength is different from the second wavelength.

Other example aspects of the present disclosure are directed to systems, methods, apparatuses, sensors, computing devices, tangible non-transitory computer-readable media, and memory devices related to the described technology.

These and other features, aspects and advantages of various embodiments will become better understood with reference to the following description and appended claims. The accompanying drawings, which are incorporated in and constitute a part of this specification, illustrate embodiments of the present disclosure, and together with the description, serve to explain the related principles.

BRIEF DESCRIPTION OF THE DRAWINGS

The foregoing aspects and many of the advantages of this application will become more readily appreciated as the same becomes better understood by reference to the following detailed description, when taken in conjunction with the accompanying drawings.

DETAILED DESCRIPTION

Figure 1A:
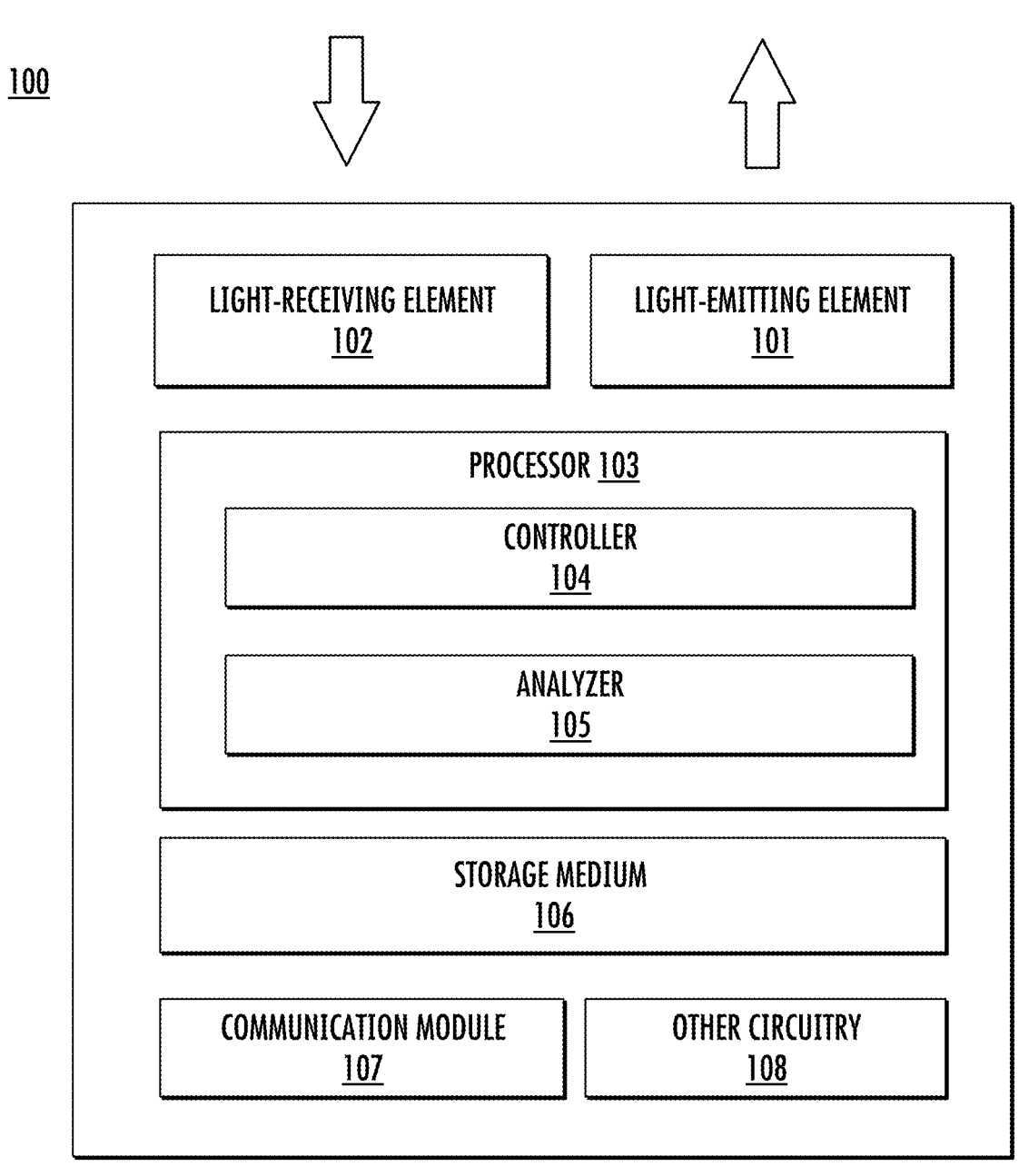
FIG. 1A shows a schematic view of an optical sensor device in accordance with one embodiment of the present disclosure.

The following embodiments accompany the drawings to illustrate the concept of the present disclosure. In the drawings or descriptions, similar or identical parts use the same reference numerals, and in the drawings, the shape, thickness, or height of the element can be reasonably expanded or reduced. The embodiments listed in the present application are only used to illustrate the present application and are not used to limit the scope of the present application. Any obvious modification or change made to the present application does not depart from the spirit and scope of the present application.

In general, an optical sensor device can be used to measure various bioinformation from a user. For example, a photoplethysmogram (PPG) is an optically obtained plethysmogram, which can be used to determine various bioinformation such as heart rate, calories, skin hydration level, blood oxygen level ($SpO_2$), and/or blood pressure, etc. In some implementations, the optical sensor device can measure the bioinformation from a user or the various conditions of an object according to the optical spectroscopy of the reflected optical signal from the user or the object. The optical sensor device can be assembled in a portable apparatus worn on the user for various activities and perform various measurements. For example, a portable apparatus with an optical sensor device can allow users to perform the skin hydration measurement of the user or the moisture measurement on an object (e.g., fruits). For another example, the optical sensor device may be included in a medical apparatus or a clinical apparatus to measure and/or monitor hydration content and/or hydration trends in tissue. The optical measurement can rely on using a light that is within the strong water absorption band (e.g., 1450 nm, 1940 nm). When performing the skin hydration level measurement, the optical sensor device emits light toward the user and penetrates the skin and underlying tissue (e.g., stratum corneum or epidermis) based on the properties of the light and the skin. The optical sensor device may then receive the reflected light as a combination of reflected, scattered, and transmitted light from the skin and underlying tissue. The reflected light can be used to determine hydration level information.

The present disclosure discloses a hydration measurement method that uses a non-invasive optical technology and a spectroscopy method that reduces computational complexity. When the hydration measurement is performed, the optical sensor device can emit at least two distinct wavelengths of light toward the object, such as a user. Since water has different absorption coefficients at each different wavelength, the object with water has different absorption coefficients at each different wavelength. The optical sensor device can receive the reflected light interacting with the object to obtain the spectroscopy at each wavelength to determine the hydration level (e.g., percentage of water) based on the analysis of the different spectroscopy.

FIG. 1A shows a schematic view of an optical sensor device 100 in accordance with one embodiment of the present disclosure. The optical sensor device 100 can be arranged in a portable apparatus (e.g., a mobile phone, a handheld instrument, an earbud, a pair of glasses, a helmet, a wristband, or a watch). The optical sensor device 100 includes a light-emitting element 101, a light-receiving element 102, a processor 103, a storage medium 106, a communication module 107, and other circuitries 108. The light-emitting element 101 is configured to emit one or more lights (e.g., SWIR lights) to an object to perform one or more tasks (e.g., proximity detection or measuring the characteristics of the object). The light-emitting element 101 can be semiconductor light-emitting devices, such as a light-emitting diode (LED), a laser diode, a vertical-cavity surface-emitting laser (VCSEL), or an organic light-emitting diode (OLED). The light-emitting element 101 can emit light corresponding to the detecting wavelength of the light-receiving element 102.

The light-receiving element 102 is configured to receive the reflected light from the object that is in proximity to the optical sensor device 100 and provide an electrical signal representing the received signal strength. The light-receiving element 102 can include a single photoelectronic device or a plurality of photoelectronic devices arranged in an array (e.g., a one-dimensional array or a two-dimensional array). The photoelectronic device can include a supporting substrate and a sensing region supported by the supporting substrate. The sensing region can include group-IV materials or group-III-V materials configured to absorb photons. The group-IV materials can include silicon (Si) or germanium (Ge), or a material compound of Si and Ge. The group-III-V materials can include Al, Ga, In, N, P, As, Sb, or any combination thereof. The supporting substrate can include a material, such as silicon (Si), that can be different from or the same as that of the sensing region. The light-receiving element 102 can detect visible light, or non-visible light according to the application.

The processor 103 is coupled to the light-emitting element 101 and the light-receiving element 102. The processor 103 includes a controller 104 and an analyzer 105. The controller 104 is configured to control the light-emitting element 101 (e.g., turn on/off, the power level, emission period, spectrum, frequency of emission, etc.) and the light-receiving element 102 (e.g., bias level, turn on/off, etc.). The analyzer 105 may include one or more analysis units for different applications, such as a skin detection unit, a bio-information calculation unit, a heart rate calculation unit, a hydration measurement unit, etc. The analyzer 105 can calculate and determine the bioinformation or the detection results of each application based on the received signal from the light-receiving element 102. The processor 103 can be implemented in numerous ways, with software and/or hardware (e.g., digital signal processor (DSP), general purpose processor, application-specific integrated circuit (ASIC), analog circuitry, digital circuitry, any combinations thereof, etc.), to perform the various functions.

The storage medium 106 is coupled to the processor 103 and may include one or more non-transitory processor-readable memories that store essential parameters and coefficients associated with the operation of the optical sensor device 100. The communication module 107 may include a wireless or wired transceiver configured to communicate with one or more devices to transmit and display the detection result over various networks, such as cellular network, PAN, LAN, MAN, and/or WAN. In one embodiment, the wireless transceiver may support Bluetooth enabled technologies such as Bluetooth Low Energy (BLE), IEEE 802.11ah, Zigbee, IEEE802.15-11, or WLAN (IEEE802.11 standard protocol). The other circuitry 108 can be any other circuitry (e.g., charging circuitry, additional processing circuitry, memory, other sensors) equipped on the optical sensor device 100.

Figure 1B:
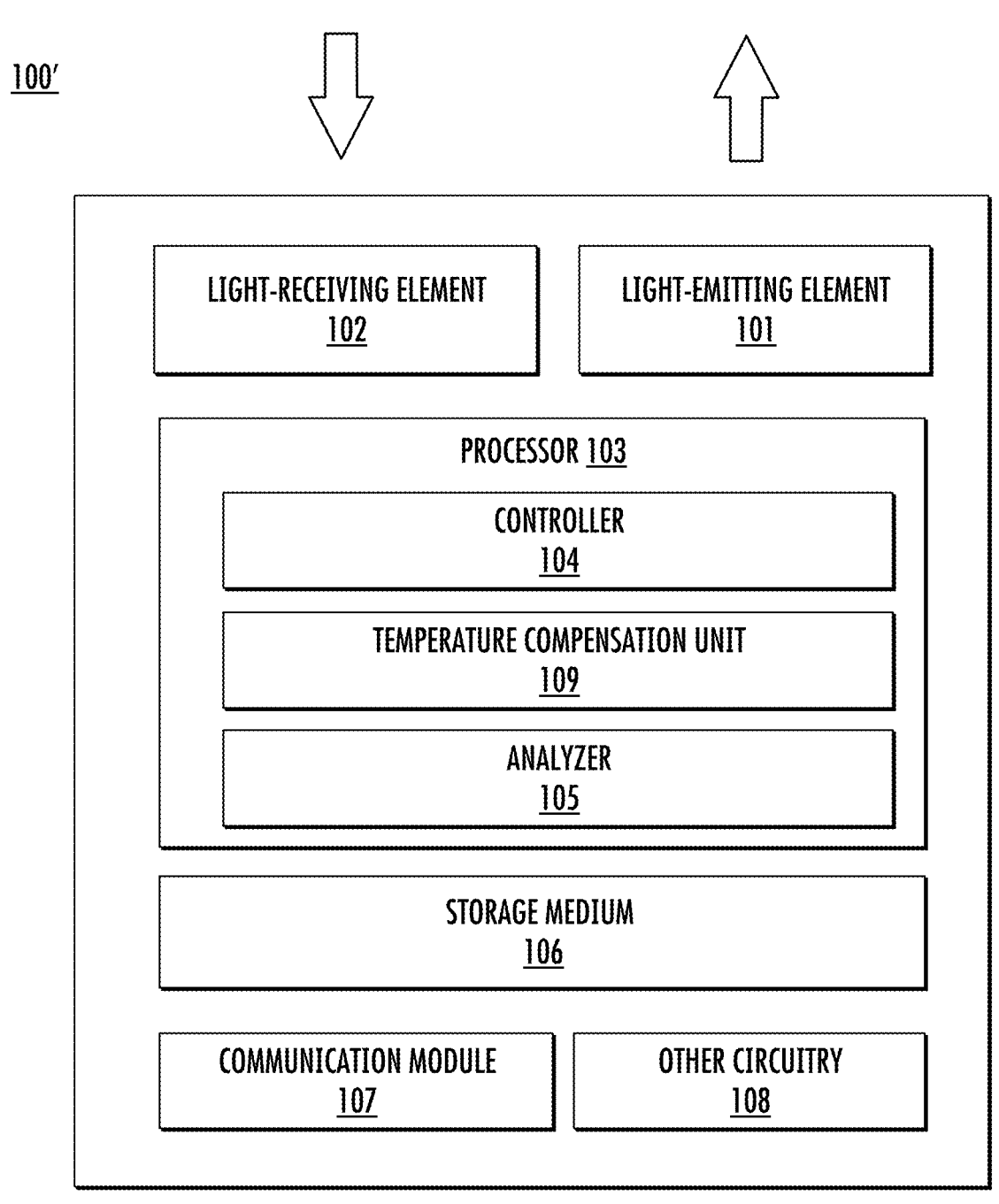
FIG. 1B shows a schematic view of an optical sensor device in accordance with another embodiment of the present disclosure.

FIG. 1B shows a schematic view of an optical sensor device 100' in accordance with another embodiment of the present disclosure. The optical power of the light-emitting element 101 and the signal strength of the received signal from the light-receiving element 102 may be affected by the ambient temperature. Variation in the signal strength of the received signal needs to be minimized so that the analyzer 105 can provide accurate detection results. The variation may come from the temperature characteristics of the light-emitting element 101 (e.g., variation in radiant flux relative to temperature) and/or the temperature characteristics of the light-receiving element 102 (e.g., variation in quantum efficiency, noises relative to temperature, etc.). Hence, it is beneficial to implement a compensation or a calibration mechanism for the signal strength of the received signal with variation over the ambient temperature to achieve accurate detection. As shown in FIG. 1B, the optical sensor device 100' is similar to the optical sensor device 100 and may further include a temperature compensation unit 109. The temperature compensation unit 109 is coupled to the analyzer 105 and configured to compensate the received signal from the light-receiving element 102 to provide a more accurate signal that is less affected by the temperature variation to the analyzer 105 for subsequent processing. Hence, the analyzer 105 can receive the compensated signal that is less affected by changes in the ambient temperature for subsequent processing to determine more accurate detection results.

Figure 2:
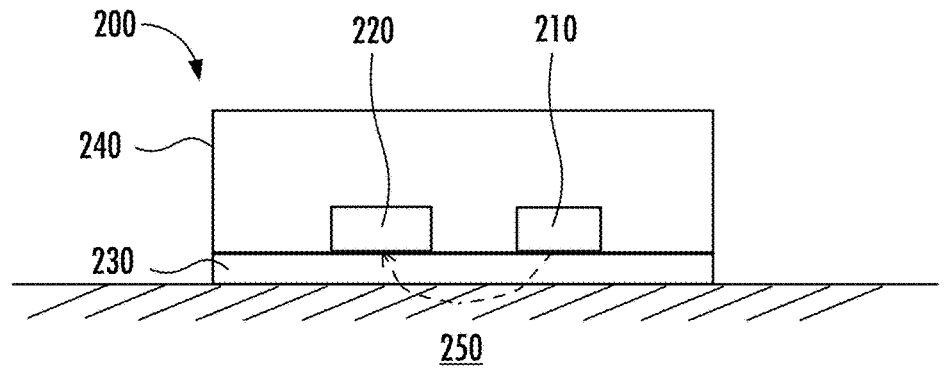
FIG. 2 shows a view of an optical sensor device measuring the hydration level of an object in accordance with one embodiment of the present disclosure.

FIG. 2 shows a view of an optical sensor device measuring the hydration level of an object in accordance with one embodiment of the present disclosure. The optical sensor device 200 includes a package body 240, at least one light-emitting element 210 and at least one light-receiving element 220 located in the package body 240, and a cover window 230 covering the package body 240 to protect the light-emitting element 210 and the light-receiving element 220 from moisture or dust. In one implementation, the cover window 230 can also be configured to set a field of view for the light-receiving element 220 and/or to focus the reflected light from the object 250. Although FIG. 2 shows one light-emitting element 210 and one light-receiving element 220, it will be understood the number of the light-emitting element and the light-receiving element may vary according to the different optical designs. The cover window 230 is transparent to light emitted and received by the optical sensor device 200. The optical sensor device 200 may be placed anywhere that can be coupled to the object (e.g., a portion of the human body). The optical sensor device 200 may be in direct contact with the object 250 to maximize transmission of emitted light into the object 250.

As shown in FIG. 2, the cover window 230 is in contact with the object 250 to detect the hydration level of the object 250. The light-emitting element 210 and the light-receiving element 220 face the object 250, such as skin, for measuring the hydration level. The light-emitting element 210 is configured to emit at least a first light at a first wavelength W1 and a second light at a second wavelength W2 toward the object 250. The light-receiving element 220 is configured to receive at least a first reflected light at a first wavelength W1 and a second reflected light at a second wavelength W2 from the object 250 for determining the hydration level information of the object 250. Since water absorption coefficients are different for the first wavelength W1 and the second wavelength W2, the spectral reflectance of the reflected lights from the object 250 would be different for the first wavelength W1 and the second wavelength W2. The absorption coefficient of water at the second wavelength W2 is higher than that at the first wavelength W1. In other words, the water absorption coefficient to the second light is higher than that to the first light. The second wavelength W2 can be longer than the first wavelength W1. The first light can be SWIR light with a wavelength in a range of 1000~1100 nm, for example, at approximately 1050 nm. The second light can be SWIR light with a wavelength in a range of 1350~1600 nm, for example, at approximately 1450 nm.)

Figure 3:
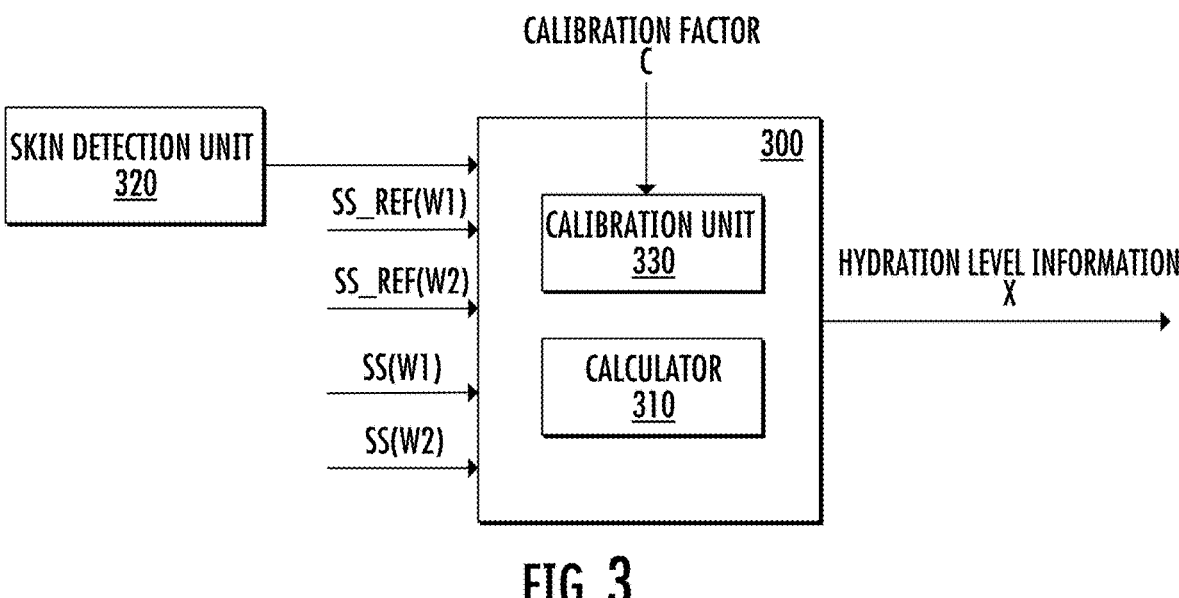
FIG. 3 illustrates a block diagram of a hydration measurement unit in accordance with one embodiment of the present disclosure.

FIG. 3 illustrates a block diagram of a hydration measurement unit in accordance with one embodiment of the present disclosure. The hydration measurement unit 300 can be implemented in the analyzer 105 and configured to perform the hydration level determination. The hydration measurement unit 300 includes a calculator 310 configured to determine and output a hydration level information X based on the input signals that are SS_Ref(W1), SS_Ref(W2), SS(W1), and SS(W2). When the calculator 310 starts to perform the hydration measurement to determine the hydration level information X, the light-emitting element 210 (as shown in FIG. 2) emits at least a first light at a first wavelength W1 and a second light at a second wavelength W2 simultaneously or interlaced. When the object is not present, the light-receiving element 220 (as shown in FIG. 2) outputs a first reference signal strength SS_Ref(W1) indicative of a received light at the first wavelength W1 and a second reference signal strength SS_Ref(W2) indicative of a received light at the second wavelength W2. The first reference signal strength SS_Ref(W1) and the second reference signal strength SS_Ref(W2) can be seen as background noises, which may be produced by the internal interference light leaked from the light-emitting element 210 through the package body without being reflected by the object, light from other light sources, or ambient light. When the object is present, the light-receiving element 220 outputs a first reflected signal strength SS(W1) indicative of a first reflected light from the object at the first wavelength W1 and the second reflected signal strength SS(W2) indicative of a second reflected light from the object at the second wavelength W2. In an implementation, the signal strengths SS_Ref(W1), SS_Ref(W2), SS(W1), SS(W2) can be represented by digital signals produced by an analog-to-digital converter (ADC) (not shown).

The hydration level information X of the object can be calculated by a mathematical method, such as a curve fitting method, which needs at least one input parameter and a plurality of fitting coefficients c[n], where n is an integer. At least one input parameter can be related to the input signals, which are SS_Ref(W1), SS_Ref(W2), SS(W1), SS(W2). Since the water absorption coefficient to the second light with the second wavelength W2 is high, the input signals regarding the second wavelength W2 are the essential factors to determine the hydration level information X. The input signals regarding the first wavelength W1 can be the factors indicative of the distance from the object. In order to obtain a suitable mathematical equation to determine the hydration level information X, an object (e.g., the user's arm) with different hydration levels can be measured by the optical sensor device to obtain several input signals related to the first wavelength W1 and the second wavelength W2, which are SS_Ref(W1), SS_Ref(W2), SS(W1), SS(W2). The different hydration levels of the object also can be measured by a commercially available equipment designed to measure skin hydration. According to the different hydration levels obtained from the commercially available skin moisture analyzer, several input parameters can be found by combining the input signals through mathematical methods (e.g., curve-fitting method) to match the corresponding hydration levels. An equation used to determine the hydration level information X can be formed by several input parameters and corresponding fitting coefficients.

An example hydration measurement for determining the hydration level information X may be the following equations:

A first adjusted signal strength SS' (W1) representing the reflected light from the object at the first wavelength W1 does not contain the background noises, and can be calculated by the following equation:

$$SS'(W1) = SS(W1) - SS\_Ref(W1).$$

A second adjusted signal strength SS' (W2) representing the reflected light from the object at the second wavelength W2 does not contain the background noises, and can be calculated by the following equation:

$$SS'(W2) = SS(W2) - SS\_Ref(W2).$$

In an implementation, at least one input parameter can be obtained by a combination of SS_Ref(W1), SS_Ref(W2), SS(W1), SS(W2), SS' (W1), and/or SS' (W2). An example of at least one input parameter can include at least one of the following expressions:

$$\exp\left(\frac{1}{SS(W1)}\right), \exp\left(\frac{1}{SS\_Ref(W1)}\right), \exp\left(\frac{1}{SS(W2)}\right), \exp\left(\frac{1}{SS\_Ref(W2)}\right),$$
$$\exp\left(\frac{1}{SS'(W1)}\right), \exp\left(\frac{1}{(SS'(W2))}\right), \frac{SS(W1)}{SS(W2)}, \frac{SS(W2)}{SS(W1)}, \frac{SS'(W1)}{SS'(W2)}, \frac{SS'(W2)}{SS'(W1)}.$$

An example calculation for hydration level information X may be determined by the equation I through a curve fitting method as follows:

$$X = c[1] \times \exp\left(\frac{1}{SS(W1)}\right) + c[2] \times \exp\left(\frac{1}{SS\_Ref(W1)}\right) +$$
$$c[3] \times \exp\left(\frac{1}{SS(W2)}\right) + c[4] \times \exp\left(\frac{1}{SS\_Ref(W2)}\right) +$$
$$c[5] \times \exp\left(\frac{1}{SS'(W1)}\right) + c[6] \times \exp\left(\frac{1}{SS'(W2)}\right) + c[7] \times \frac{SS(W1)}{SS(W2)} +$$
$$c[8] \times \frac{SS(W2)}{SS(W1)} + c[9] \times \frac{SS'(W1)}{SS'(W2)} + c[10] \times \frac{SS'(W2)}{SS'(W1)} + c[11].$$

Figure 4:
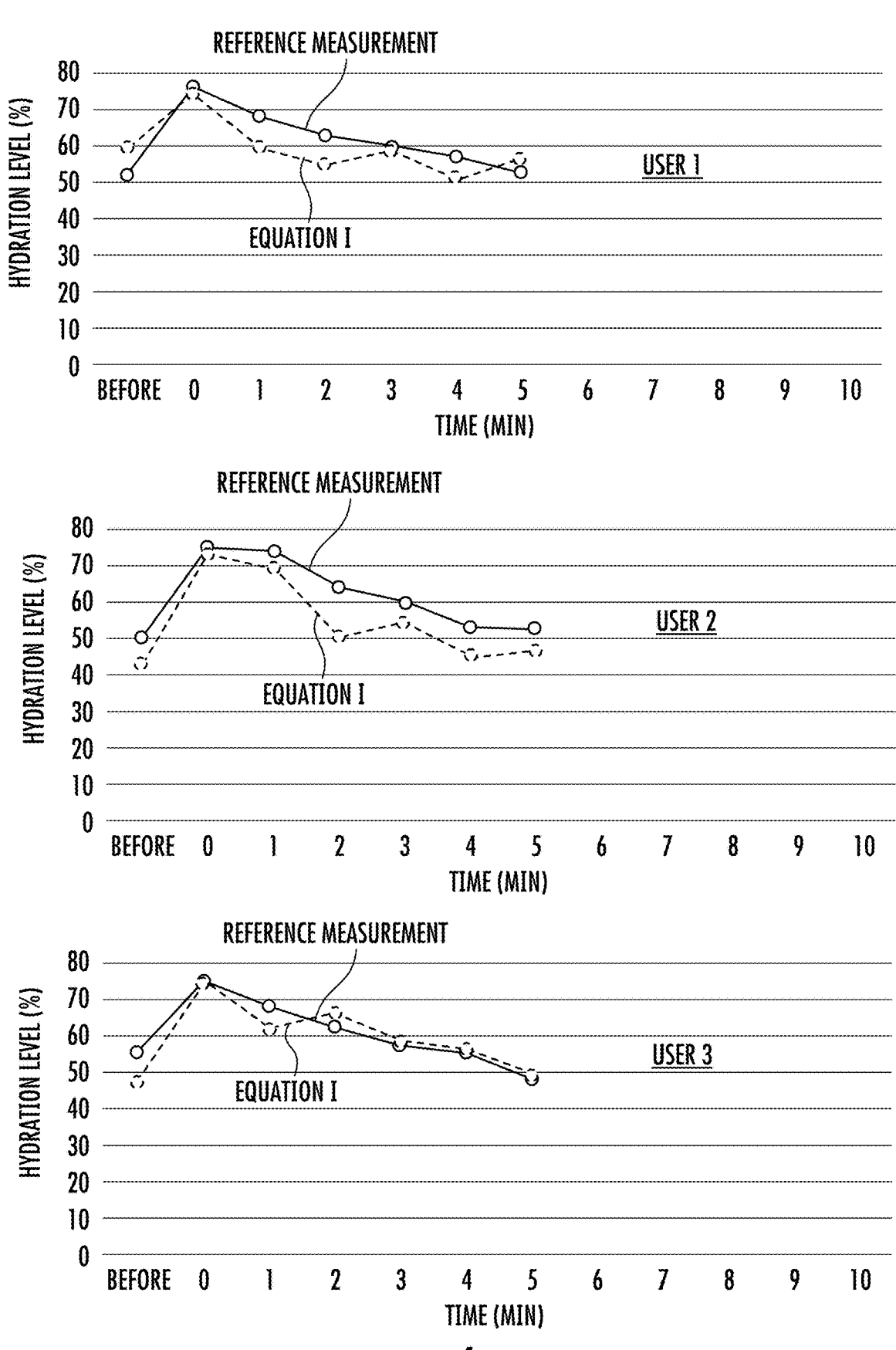
FIG. 4 illustrates graphs of hydration level calculated by equation I versus hydration level measured by equipment for different users in accordance with one embodiment of the present disclosure.

Thus, the method of this disclosure is easy to implement and does not require to know the optical properties of the object in advance for hydration measurement. FIG. 4 illustrates graphs of hydration level calculated by equation I versus hydration level measured by equipment for different users in accordance with one embodiment of the present disclosure. The equipment could be a commercially available skin moisture analyzer that measures hydration level based on the capacitance measurement of a dielectric medium. The graph shows the change of hydration level, expressed as a percentage, at the same skin location over five minutes after applying water to the skin. 0 minute on the X-axis indicates that water has just been applied to the skin, and the hydration level per minute is displayed at points 0 to 5 on the X-axis. There are two curves in each graph for different users, one curve denoted as reference measurement is the result of using equipment to measure the hydration level, and another curve denoted as equation I is the calculation result of equation I. It can be observed from each graph of different users that the hydration level obtained by equation I is very close to the value measured by the equipment. The fitting coefficients c[n] may be c[1, 2 . . . , 11]=[−44.044, 518.419, 55.3, 32.588, −44.349, −38.457, −9.473, −3328.724, 0, 0, −52.190].

In another embodiment, except for the input signals that are SS_Ref(W1), SS_Ref(W2), SS(W1), and SS(W2), the calculator 310 can receive the output of the skin detection unit 320 which is implemented in the analyzer 105 for skin detection. The calculator 310 can determine whether to process the hydration measurement according to the output of the skin detection unit 320 to save power consumption. In an implementation, if the output of the skin detection unit indicates the presence of the skin, which indicates the object is a human, the calculator 310 processes the calculation for the hydration level information. If the output of the skin detection unit 320 indicates the absence of the skin, which indicates the object is not a human, the calculator 310 will not process the calculation for the hydration level information.

The input signals SS_Ref(W1), SS_Ref(W2), SS(W1), and SS(W2) may be nonconsistency between different optical sensor devices due to the optoelectrical characteristic difference. The nonconsistency of the input signals may cause the nonconsistency of hydration level information X between different optical sensor devices operated for the same object. In an implementation, the hydration measurement unit 300 may optionally include a calibration unit 330, which is configured to calibrate the input signals SS_Ref (W1), SS_Ref(W2), SS(W1), and SS(W2) to eliminate the effect from the optoelectrical characteristic variation of the optical sensor device. The calibration unit 330 can calibrate at least one of the input signals by a calibration factor C. Then, the calibrated input signals are transmitted to the calculator 310 to obtain more accurate hydration level information. The calibration factor C can be measured during the manufacturing process and stored in the calibration unit 330 or the storage medium 106 (refer to FIG. 1A). In an embodiment, the calibration process can be performed by a function input signal/C or input signal×C.

In an implementation, during the manufacturing process, a reference object made of silicone-based material or 1-Propanol and a test optical sensor device can be prepared to obtain the calibration factor C. The test optical sensor device performs optical measurements on the reference object to obtain the reference input signals SS_Ref(W1)_0, SS_Ref (W2)_0, SS(W1)_0, and SS(W2)_0. Then, each manufactured optical sensor device performs optical measurements on the reference object to obtain measured input signals SS_Ref(W1), SS_Ref(W2), SS(W1), and SS(W2). The calibration factor C can be obtained by comparing the reference input signals SS_Ref(W1)_0, SS_Ref(W2)_0, SS(W1)_0 with the measured input signals SS_Ref(W1), SS_Ref(W2), SS(W1) and SS(W2).

In an implementation, the calibration unit 330 calibrates SS(W2) and SS_Ref(W1) by the calibration factor C for more accurate hydration level information. Since the absorption coefficient of water at the second wavelength W2 is higher than that at the first wavelength W1, the calibration unit 330 calibrates SS(W2) without calibrating SS(W1), which is sufficient to obtain more accurate hydration level information. The calibration unit 330 calibrates SS_Ref (W1) by the calibration factor C without calibrating SS_Ref (W2), which is sufficient to eliminate the effect from the optoelectrical characteristic variation of the optical sensor device.

Figure 5:
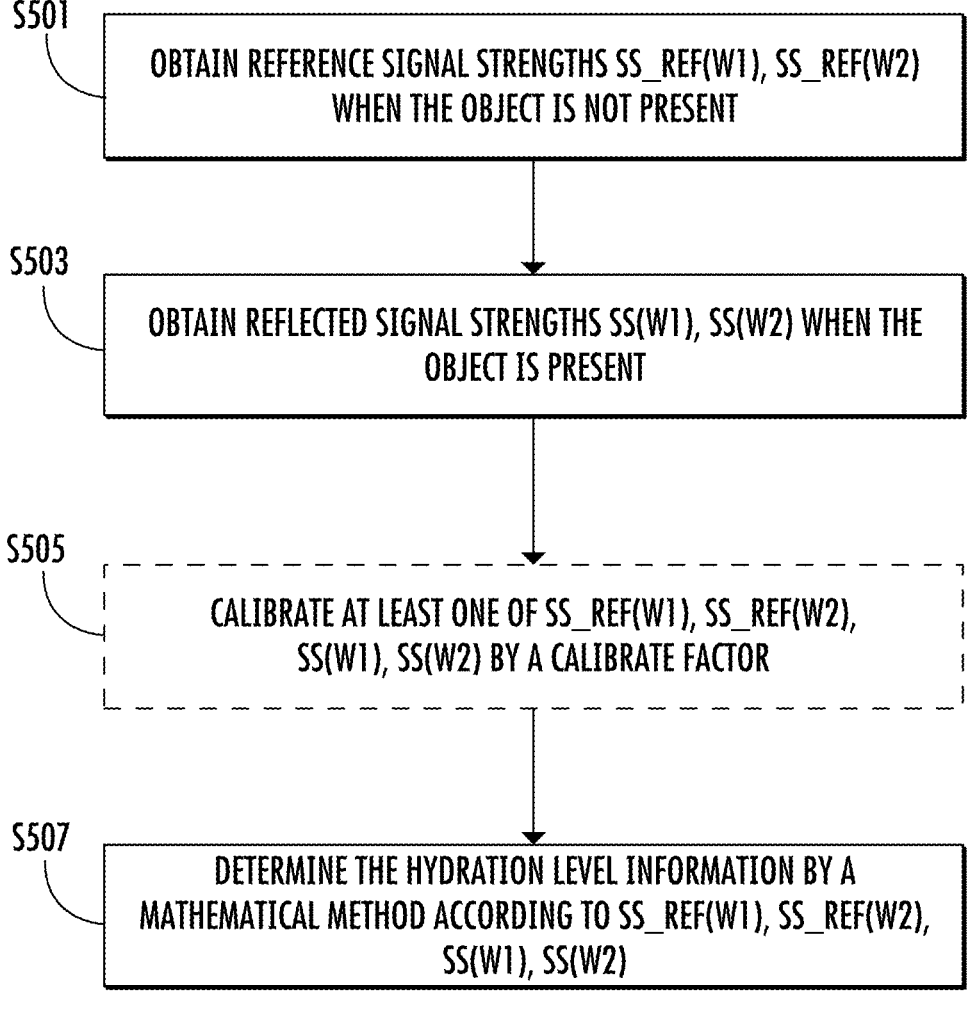
FIG. 5 illustrates a flow of a hydration measurement in accordance with one embodiment of the present disclosure.

FIG. 5 shows a hydration measurement flow of an optical sensor device in accordance with one embodiment of the present disclosure. The hydration measurement is performed by a hydration measurement unit. As shown in step S501, when the hydration measurement starts, the light-emitting element emits a first light at a first wavelength W1 and a second light at a second wavelength W2. The hydration measurement unit obtains the first reference signal strength SS_Ref(W1) at the first wavelength W1 and a second reference signal strength SS_Ref(W2) at the second wavelength W2 from the light-receiving element when the object is not present. As shown in step S503, when the object is present, the hydration measurement unit obtains the first reflected signal strength SS(W1) at the first wavelength W1 and the second reflected signal strength SS(W2) at the first wavelength W2. Then, as shown in step 507, the hydration measurement unit calculates and determines the hydration level information by a mathematical method according to SS_Ref(W1), SS_Ref(W2), SS(W1), SS(W2). Optionally, as shown in step S505, before calculating step for hydration level information, a calibration unit calibrates at least one of the signals SS_Ref(W1), SS_Ref(W2), SS(W1), SS(W2) and transmits the calibrated signals to perform the calculation for the hydration level information.

Figure 6A:
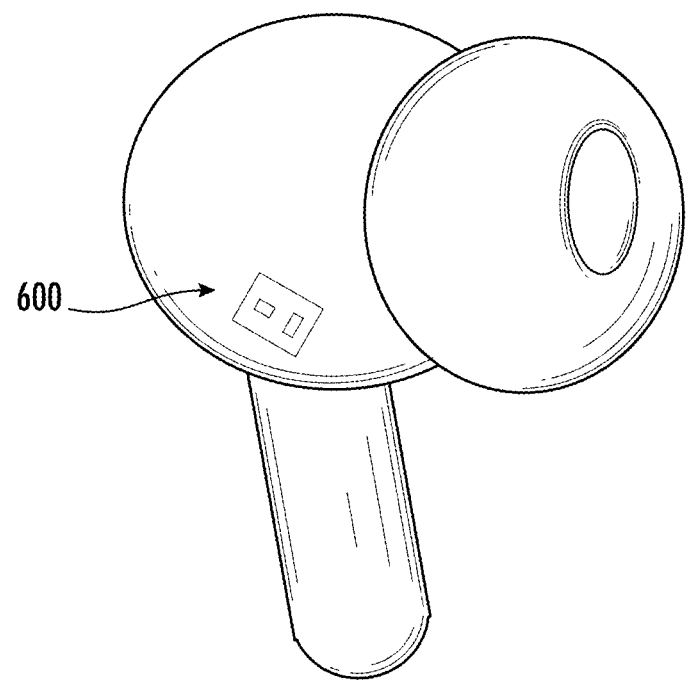
FIG. 6A shows an earbud including an optical sensor device in accordance with one embodiment of the present disclosure.
Figure 6B:
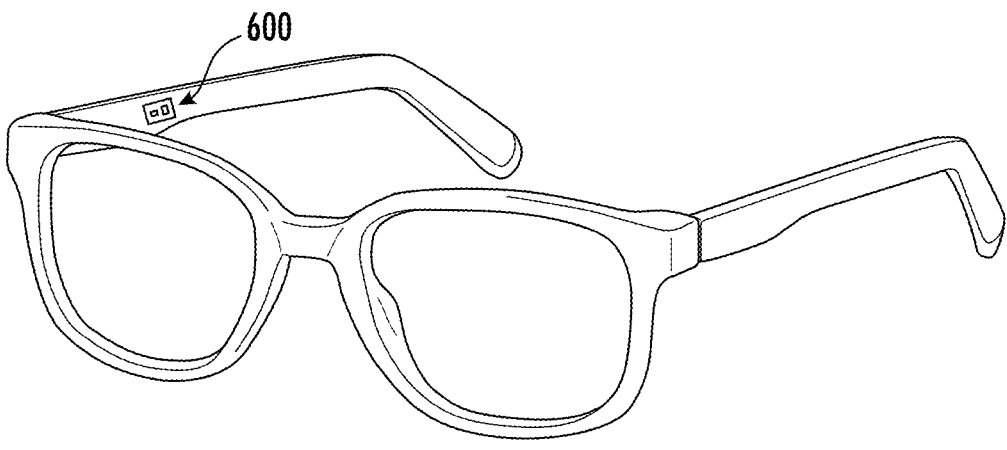
FIG. 6B shows a pair of glasses including an optical sensor device in accordance with one embodiment of the present disclosure.

FIGS. 6A~6B show different wearable/portable devices including the optical sensor device in accordance with different embodiments of the present disclosure. FIG. 6A shows an earbud including an optical sensor device 600. When the user wears the earbud to listen to music or communicate, the optical sensor device 600 contacts the skin of the user and can be configured to measure various bioinformation at the same time. FIG. 6B shows a pair of glasses including an optical sensor device 600. When the user wears a pair of glasses, the optical sensor device 600 contacts the skin of the user and can be configured to measure various bioinformation at the same time. The optical sensor device 600 can be one of the aforementioned optical sensor devices. FIGS. 6A~6B show two examples of wearable/portable devices, however suitable wearable/portable devices such as helmet, wristband, watch, ring, can be installed the optical sensor device to measure various bioinformation.

Figure 7:
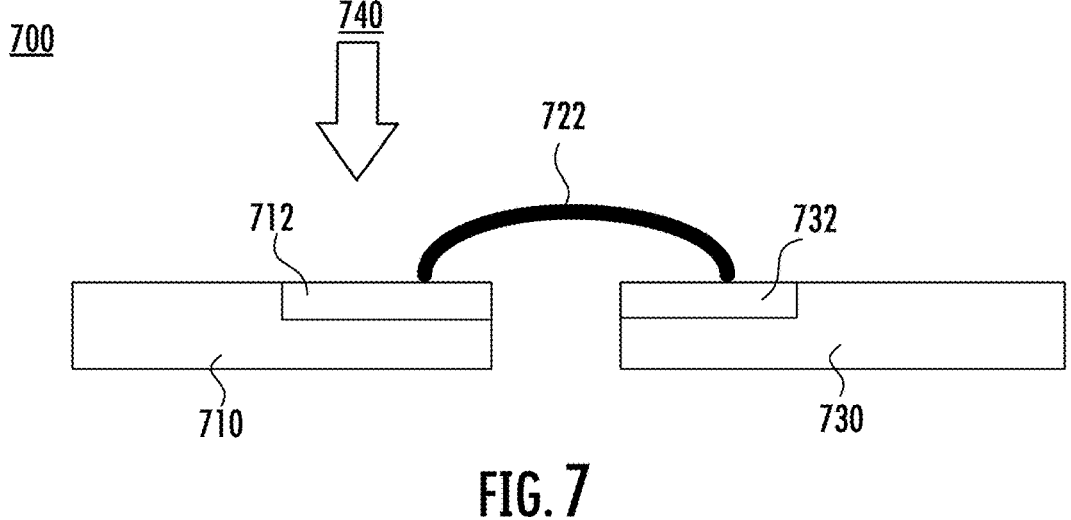
FIG. 7 shows a light-receiving element in accordance with one embodiment of the present disclosure.

FIG. 7 illustrates a light-receiving element 700, which can be an example of the light-receiving element 102, 220. A light-receiving element 700 includes a first substrate 710 and a second substrate 730. The first substrate 710 includes a sensing area 712 (e.g., III-V material) that is electrically coupled to sensing circuitry 732 (e.g., CMOS circuitry) of the second substrate 730 via wire(s) 722 (e.g., wire-bonded).

Figure 8:
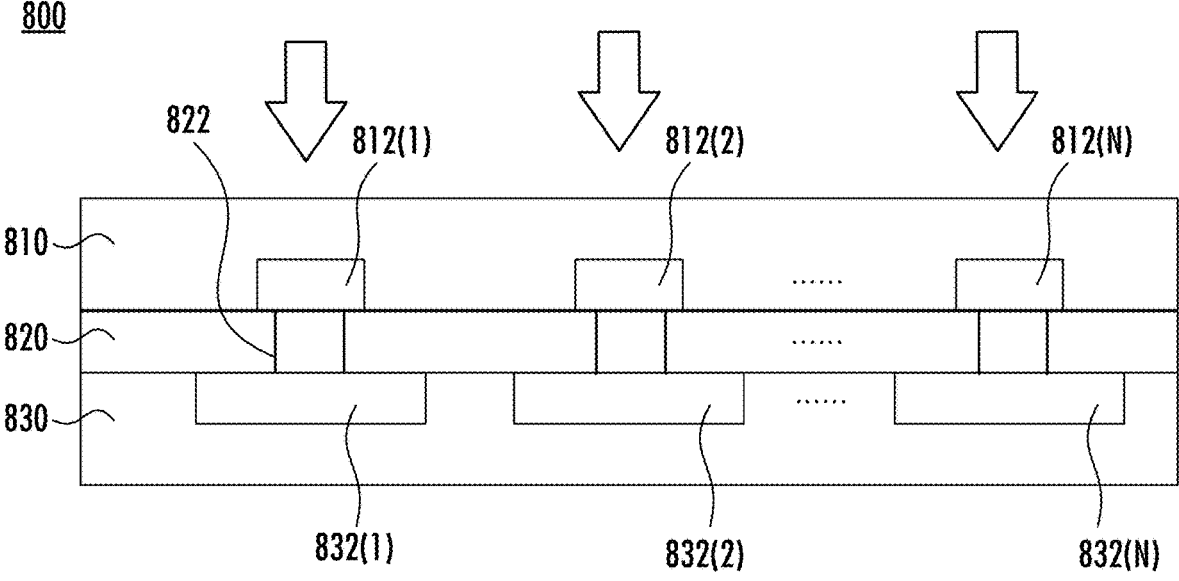
FIG. 8 illustrates a light-receiving element in accordance with another embodiment of the present disclosure.

FIG. 8 illustrates a light-receiving element 800, which can be another example of the light-receiving element 102, 220. The light-receiving element 800 includes a first substrate 810 and a second substrate 830, which can both be silicon substrate. The first substrate 810 and the second substrate 830 are wafer-bonded via a bonding interface 820 (e.g., oxide or any other suitable materials). The first substrate 810 includes multiple sensing areas 812(1)~812(N), where N is a positive integer. In some implementations, the multiple sensing areas 812(1)~812(N) may be comprised of germanium that is deposited on silicon forming the first substrate 810. The second substrate 730 includes multiple corresponding circuitry areas 832(1)~832(N). The multiple sensing areas 812(1)~812(N) and the multiple corresponding circuitry areas 832(1)~832(N) are electrically coupled through the bonding interface 820 via wires 822.

Various means can be configured to perform the methods, operations, and processes described herein. For example, any of the systems and apparatuses (e.g., optical sensor devices and related circuitry) can include unit(s) and/or other means for performing their operations and functions described herein. In some implementations, one or more of the units may be implemented separately. In some implementations, one or more units may be a part of or included in one or more other units. These means can include processor(s), microprocessor(s), graphics processing unit(s), logic circuit(s), dedicated circuit(s), application-specific integrated circuit(s), programmable array logic, field-programmable gate array(s), controller(s), microcontroller(s), and/or other suitable hardware. The means can also, or alternately, include software control means implemented with a processor or logic circuitry, for example. The means can include or otherwise be able to access memory such as, for example, one or more non-transitory computer-readable storage media, such as random-access memory, read-only memory, electrically erasable programmable read-only memory, erasable programmable read-only memory, flash/other memory device(s), data register(s), database(s), and/or other suitable hardware.

As used herein, the terms such as "first", "second", "third", etc. describe various elements, components, regions, layers and/or sections, these elements, components, regions, layers and/or sections should not be limited by these terms. These terms may be only used to distinguish one element, component, region, layer, section, signal, or operation from another. The terms such as "first", "second", "third", etc. when used herein do not imply a sequence or order unless clearly indicated by the context. The terms "light-receiving", "light-detecting", "light-sensing" and any other similar terms can be used interchangeably.

Aspects of the disclosure have been described in terms of illustrative embodiments thereof. Numerous other embodiments, modifications, and/or variations within the scope and spirit of the appended claims can occur to persons of ordinary skill in the art from a review of this disclosure. Any and all features in the following claims can be combined and/or rearranged in any way possible. Accordingly, the scope of the present disclosure is by way of example rather than by way of limitation, and the subject disclosure does not preclude inclusion of such modifications, variations or additions to the present subject matter as would be readily apparent to one of ordinary skill in the art. Moreover, terms are described herein using lists of example elements joined by conjunctions such as "and," "or," "but," etc. It should be understood that such conjunctions are provided for explanatory purposes only. Lists joined by a particular conjunction such as "or," for example, can refer to "at least one of" or "any combination of" example elements listed therein. Also, terms such as "based on" should be understood as "based at least in part on".

Those of ordinary skill in the art, using the disclosures provided herein, will understand that the elements of any of the claims discussed herein can be adapted, rearranged, expanded, omitted, combined, or modified in various ways without deviating from the scope of the present disclosure.

While the disclosure has been described by way of example and in terms of a preferred embodiment, it is to be understood that the disclosure is not limited thereto. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. An optical sensor device for determining a hydration level information of an object, comprising:
   a light-emitting element configured to emit a first light at a first wavelength and a second light at a second wavelength;
   a light-receiving element configured to receive a first reflected light at the first wavelength and a second reflected light at the second wavelength from the object; and
   an analyzer configured to perform a hydration measurement to determine the hydration level information, wherein performing the hydration measurement comprises:

obtaining a first reference signal strength at the first wavelength and a second reference signal strength at the second wavelength from the light-receiving element when the object is not present;
   obtaining a first signal strength of the first reflected light and a second signal strength of the second reflected light from the light-receiving element when the object is present; and
   determining the hydration level information based on the first reference signal strength, the second reference signal strength, the first signal strength, and the second signal strength.

2. The optical sensor device of claim 1, wherein performing the hydration measurement further comprises calibrating at least one of the first reference signal strength, the second reference signal strength, the first signal strength, and the second signal strength before determining the hydration level information.

3. The optical sensor device of claim 2, wherein the calibrating step uses a calibration factor to calibrate at least one of the first reference signal strength, the second reference signal strength, the first signal strength, and the second signal strength.

4. The optical sensor device of claim 1, wherein the first wavelength is different from the second wavelength.

5. The optical sensor device of claim 1, wherein the hydration level information is determined by a mathematical method.

6. The optical sensor device of claim 5, wherein the mathematical method is a curve fitting method.

7. The optical sensor device of claim 1, wherein the first wavelength and the second wavelength are within a short-wavelength infrared (SWIR) wavelength range.

8. The optical sensor device of claim 1, wherein the first wavelength is at approximately 1050 nm.

9. The optical sensor device of claim 1, wherein the second wavelength is at approximately 1450 nm.

10. The optical sensor device of claim 1, wherein an absorption coefficient of water at the second wavelength is higher than that at the first wavelength.

11. A method of hydration measurement of an optical sensor device for an object, comprising:
   receiving, by a hydration measurement unit, a first reference signal strength at a first wavelength and a second reference signal strength at a second wavelength from a light-receiving element when the object is not present;
   receiving, by the hydration measurement unit, a first signal strength at the first wavelength and a second signal strength at the second wavelength from the light-receiving element when the object is present; and
   determining, by the hydration measurement unit, a hydration level information based on the first reference signal strength, the second reference signal strength, the first signal strength, and the second signal strength.

12. The method of claim 11, further comprising calibrating at least one of the first reference signal strength, the second reference signal strength, the first signal strength, and the second signal strength before the determining step.

13. The method of claim 12, wherein the calibrating step uses a calibration factor to calibrate at least one of the first reference signal strength, the second reference signal strength, the first signal strength, and the second signal strength.

14. The method of claim 11, wherein the hydration level information is determined by a mathematical method.

15. The method of claim 14, wherein the mathematical method is curve fitting method.

16. The method of claim 11, wherein the first wavelength and the second wavelength are within a short-wavelength infrared (SWIR) wavelength range.

17. The method of claim 11, wherein the first wavelength is at approximately 1050 nm.

18. The method of claim 11, wherein the second wavelength is at approximately 1450 nm.

19. The method of claim 11, wherein an absorption coefficient of water at the second wavelength is higher than that at the first wavelength.

20. The method of claim 11, wherein the first wavelength is different from the second wavelength.

* * * * *